United States Patent [19]

Corth

[11] 4,246,905

[45] Jan. 27, 1981

[54] LOW-PRESSURE MERCURY-VAPOR DISCHARGE LAMP FOR TREATMENT OF HYPERBILIRUBINEMIA AND METHOD

[75] Inventor: Richard Corth, Nutley, N.J.

[73] Assignee: Westinghouse Electric Corp., Pittsburgh, Pa.

[21] Appl. No.: 20,596

[22] Filed: Mar. 14, 1979

[51] Int. Cl.³ ............................................. A61N 5/00
[52] U.S. Cl. ............................ 128/395; 252/301.4 P; 313/487
[58] Field of Search ............... 128/395, 396, 397, 398; 313/487; 252/301.4 P

[56] References Cited

U.S. PATENT DOCUMENTS

| 3,658,068 | 4/1972 | McNall | 128/395 |
| 4,079,287 | 3/1978 | Soules et al. | 252/301.4 P |

OTHER PUBLICATIONS

"Prevention of Hyperbilirubinemia of Prematurity by Photo therapy" Luccy, M.D. et al., Pediatrics, vol. 41 No. 6, Jun. 1968 pp. 1047-1054.
"Effect of Blue Light on Hyperbilirubinemia", Broughton et al., Archives of Diseases in Childhood, vol. 40, 1965, pp. 666-671.

*Primary Examiner*—William E. Kamm
*Assistant Examiner*—J. L. Kruter
*Attorney, Agent, or Firm*—R. S. Lombard

[57] ABSTRACT

A low-pressure mercury-vapor discharge lamp combination for phototherapeutic treatment of infantile hyperbilirubinemia. The lamp combination includes the standard hollow elongated envelope having a coating of selected phosphors carried as a layer on the inner surface thereof. The coating of selected phosphors substantially comprises a blue-radiating alkaline-earth metal halophosphate activated with divalent europium and a second phosphor with a color output that falls within a predetermined area of an xy-C.I.E. diagram with the weight ratio of the europium-activated alkaline-earth metal halophosphate to the second phosphor being from about 90:10 to 85:15. This lamp combination substantially eliminates any tendency of the blue-radiation of the alkaline-earth metal halophosphate to produce nausea in certain attendant individuals.

10 Claims, 2 Drawing Figures

LOW-PRESSURE MERCURY-VAPOR DISCHARGE LAMP FOR TREATMENT OF HYPERBILIRUBINEMIA AND METHOD

BACKGROUND OF THE INVENTION

This invention relates to low-pressure mercury-vapor discharge lamps, and in particular, those used for phototherapeutic treatment of infantile hyperbilirubinemia, which is a condition occurring in newborn infants where bilirubin is present in high concentrations such that there is significant red cell destruction.

A method of treating hyperbilirubinemia is disclosed in U.S. Pat. No. 3,658,068 dated Apr. 25, 1972 issued to J. W. McNall and assigned to the present assignee. This patent discloses that a lamp combination comprising a low-pressure mercury-vapor discharge device incorporating a phosphor of alkaline-earth metal halophosphate activated by divalent europium is particularly useful in the treatment of hyperbilirubinemia. This patent shows that utilizing the lamp combination described is effective in the treatment of hyperbilirubinemia because of concentration of the radiated energy in a portion of the spectrum which causes decomposition of the bilirubin constituent. The alkaline-earth metal halophosphate phosphors are highly absorptive of ultraviolet radiant energy, which energy is converted and re-emitted as a narrow band blue emission. The patent teaches that $Sr_3(PO_4)_3Cl:Eu^{++}$ wherein the gram-atom ratio of europium to europium plus strontium is about 0.015 is the preferable composition from the standpoint of best efficiency of emission.

The foregoing patent gives an example of the treatment process in which about ten 20 watt lamps incorporating the blue-emitting phosphor are disposed in a unitary fixture which has an ultraviolet absorptive cover to prevent any possible exposure of the infant to ultraviolet radiation. The eyes of the infant to be treated are covered with a suitable light shield. The infant is disposed a distance from the fixture such that the energy level at the peak wavelength reaching the infant is about 90 microwatts per square centimeter per nanometer.

An alternative apparatus for phototherapeutic treatment of hyperbilirubinemia is disclosed in U.S. Pat. No. 3,822,706 dated July 9, 1974, issued to Simone et al. The Simone patent discloses a light comprising a neon bulb, which emits light radiation in the blue portion of the visible spectrum and having a filter means for absorption of ultraviolet radiation before transmission of the light to the infant. The neon light is mounted on a housing open at one end for permitting the head of the infant to extend outside of the housing. A shield is mounted on one end of the housing for shielding the infant's head from the light emitted from the neon lamp.

It has been found that occasionally, certain attendant individuals, such as the nurses, may experience a feeling of nausea, apparently as a result of continuously viewing the blue radiation emitted by a lamp operating at the optimum portion of the spectrum for phototherapeutic treatment of hyperbilirubinemia. Apparently, this is a visual phenomenon.

SUMMARY OF THE INVENTION

There is provided a lamp combination for phototherapeutic treatment of hyperbilirubinemia, including a low-pressure mercury-vapor discharge lamp having a hollow elongated vitreous envelope with electrodes operatively disposed proximate the ends thereof. The envelope encloses a discharge sustaining atmosphere comprising mercury and an inert, ionizable starting gas.

The improvement in the combination is a coating of selected phosphors carried as a layer on the inner surface of the envelope substantially comprising blue-radiating alkaline-earth metal halophosphate activated by divalent europium and a phosphor with a color output that falls within an area of an xy-C.I.E. coordinate diagram, said area constituting a trapezium with corners at xy-C.I.E. coordinates (0.423, 0.370), (0.370, 0.410), (0.445, 0.550), (0.515, 0.484) with a weight ratio of alkaline-earth metal halophosphate activated by divalent europium to the second phosphor being from about 90:10 to 85:15. When treating infantile hyperbilirubinemia with such a lamp, any tendency of the blue emission of the europium-activated alkaline-earth metal halophosphate to produce nausea in certain attendant individuals is substantially eliminated without appreciably affecting the efficacy of the treatment process.

BRIEF DESCRIPTION OF THE DRAWINGS

For a better understanding of the invention, reference may be had to the exemplary embodiment shown in the accompanying drawings, in which.

DESCRIPTION OF THE PREFERRED EMBODIMENT

Figure 1:
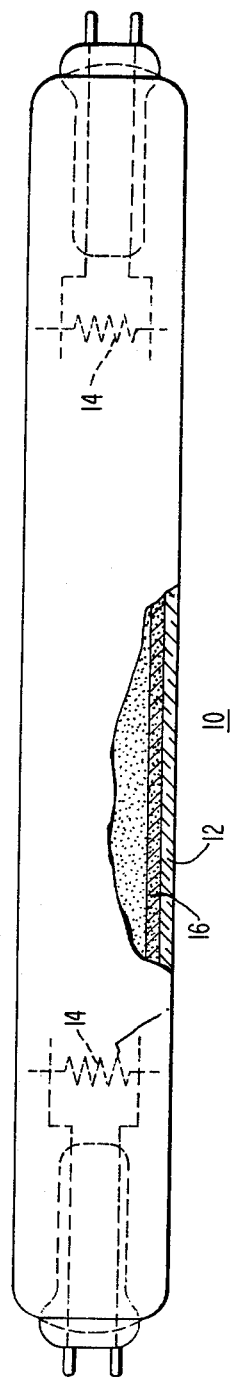
FIG. 1 is an elevational view, partly in section of a low-pressure mercury-vapor lamp showing the coating of selected phosphors carried as a layer on the inner surface of the lamp envelope; and, FIG. 2 is an xy-C.I.E. coordinate diagram with a shaded area indicating the color of the second added phosphor and showing the shift in color produced by the present treatment lamp in comparison to the color of the prior art treatment lamp.

In FIG. 1 there is shown a low-pressure mercury-vapor discharge lamp 10 for phototherapeutic treatment of infantile hyperbilirubinemia. The lamp includes a hollow elongated vitreous envelope 12 with electrodes 14 operatively disposed proximate the ends thereof. The envelope 12 encloses a discharge sustaining atmosphere comprising mercury and a small charge of inert ionizable starting gas, such as 2.2 l torrs of argon. The lamp described thus far is conventional.

The improvement comprises a coating of selected phosphors carried as a layer 16 on the inner surface of the envelope 12. The layer 16 of selected phosphors substantially comprises blue-radiating alkaline-earth metal halophosphate activated with divalent europium and a second phosphor with a color output that falls within an area of the xy-C.I.E. coordinate diagram shown as the shaded area in FIG. 2. The area constitutes a trapezium with corners corresponding to xy-C.I.E. coordinates (0.423, 0.370), (0.370, 0.410), (0.445, 0.550), (0.515, 0.484). The europium-activated alkaline-earth metal halophosphate may be any one or a combination of the alkaline-earth metal halophosphates referred to in the aforesaid U.S. Pat. No. 3,658,068. The second phoshor, for example, may be a standard, commerical halophosphate, such as a warm white halophosphate having a general constituent formulation of $3Ca_3(PO_4)_2 \cdot Ca(F,Cl)_2 : 0.175Mn : 0.015Sb$ with xy-C.I.E. coordinates of $x = 0.440$ and $y = 0.403$. The weight ratio of europium-activated alkaline-earth metal halophosphate to the second phosphor should be from about 90:10 to 85:15.

Figure 2:
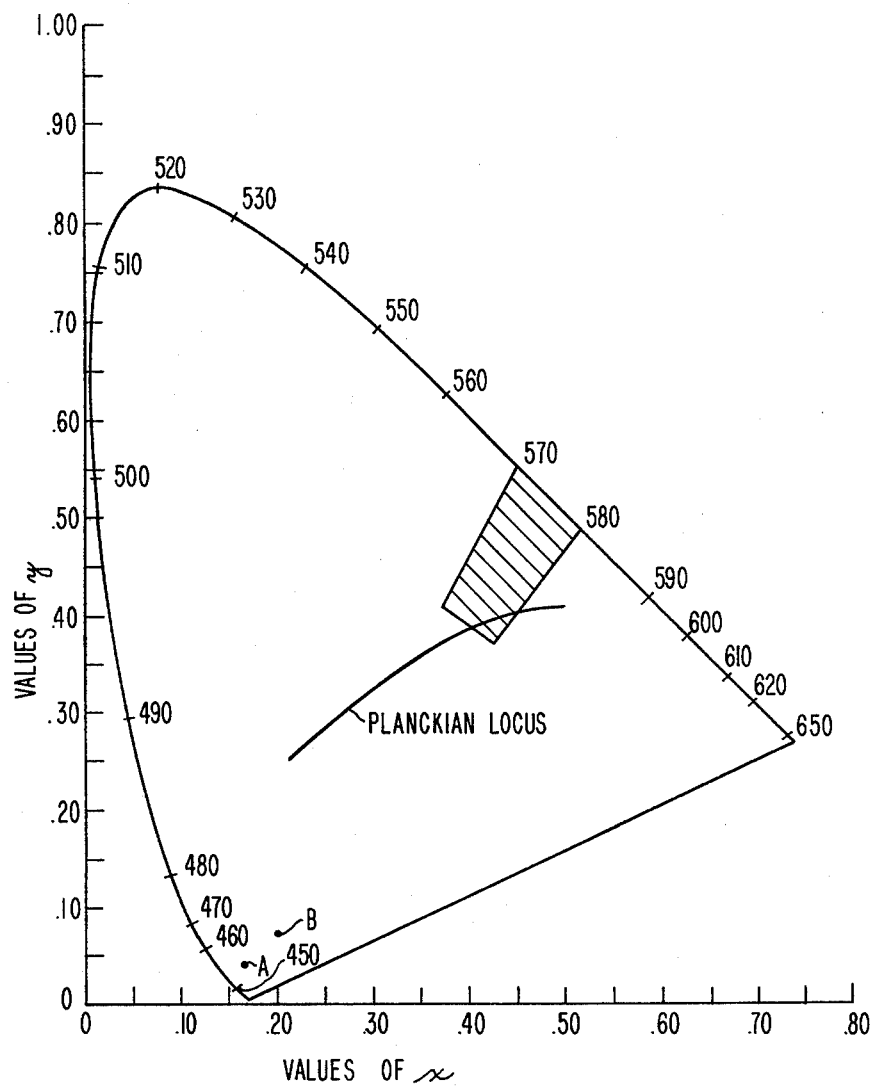

While the teachings of the present invention are applicable to low-pressure mercury-vapor discharge lamps of varying size and designed wattage input, a specific example of a lamp constructed in accordance with the present invention is a 20 watt lamp which is about 24 inches long and about 1½ inches in diameter. The mercury discharge primarily produces 254 nanometer radiation which excites the selected phosphors of the coating layer 16 to luminescence. Preferably, the coating is composed of 90% strontium chlorophosphate phosphor activated with divalent europium, with the divalent europium in an amount such that the gram-atom ratio of europium to europium plus strontium is 0.015, although this ratio may vary from about 0.150 to 0.003, and 10% of the previously described warm white halophosphate phosphor. This coating is applied to the inner surface of the envelope 14 as a point in a manner as is well known in the art, such as described in U.S. Pat. No. 3,833,392, dated Sept. 3, 1974, issued to Repsher et al. The amount of phosphor which is used is subject to considerable variation. It will, however, normally require from about 4 to 6 milligrams of the selected phosphors per square centimeter of coated area, and preferably require about 4.9 milligrams per square centimeter. The lamp described in this example gives a color output having chromaticity coordinates of $x=0.197$ and $y=0.078$ and identified as "B" in FIG. 2 compared to the prior art treatment lamp having coordinates $x=0.157$ and $y=0.047$ and identified as "A" in FIG. 2. As can be seen from the chromaticity diagram in FIG. 2, there is a significant shift from the periphery of the diagram utilizing the lamp of the present invention. The resultant emission from this lamp nevertheless still closely matches the optimum portion of the spectrum needed for the phototherapy. This shift in color appearance from the blue apearance of the prior art treatment lamp substantially eliminates any tendency to produce nausea in certain attendant individuals that may occur with the prior art treatment lamp. Measurements taken of this lamp indicate that the desired energy in the phototherapeutic portion of the spectrum is decreased by less than ten percent, as compared to the prior art treatment lamp.

By utilizing the lamp of the present invention, there results an improved method of in vivo treatment of infants having hyperbilirubinemia. The method comprises irradiating the infant subject with the emission produced by a lamp combination comprising at least one low-pressure mercury-vapor discharge device 10 having a coating 16 of selected phosphors as previously described, and shielding the eyes of the infant subject during the irradiation.

While a warm white halophosphate is preferred as the added material due to its efficient output and desired emission color, other phosphors having an output which fall within the shaded area of FIG. 2 may be substituted therefor. As an example, the added phosphor may be a white emitting calcium halphosphate having a general constituent formulation of $3Ca_3(PO_4)_2\cdot(CaF)_2:0.130Mn:0.015Sb$ with xy-C.I.E. coordinates of $x=0.410$, $y=0.390$. A yellow emitting calcium halophosphate may also be substituted for the preferred warm white material. The yellow emitting phosphor has a general constituent formulation of $3Ca_3(PO_4)_2\cdot CaF_2:0.142Mn:0.015Sb$ with xy-C.I.E. coordinates of $x=0.435$ and $y=0.435$. Other known phosphors having the specified emission requirements may be substituted therefor.

I claim:

1. In combination with a low-pressure mercury-vapor discharge lamp for phototherapeutic treatment of infantile hyperbilirubinemia, said lamp including a sealed tubular elongated vitreus envelope having electrodes operatively disposed proximate the ends thereof, said envelope enclosing a discharge sustaining atmosphere comprising mercury and inert ionizable starting gas, the improvement which comprises:
   a coating of selected phosphors carried as a layer on the inner surface of said envelope substantially comprising blue-radiating alkaline-earth metal halophosphate activated with divalent europium and a second phosphor with a color output that falls within an area of the xy-C.I.E. coordinate diagram, said area constituting a trapezium with corners at xy-C.I.E. coordinates (0.423, 0.370), (0.370, 0.410), (0.445, 0.550), (0.515, 0.484), with a weight ratio of said europium-activated alkaline-earth metal halophosphate to said second phosphor being from about 90:10 to 85:15, whereby any tendency of the blue emission of said europium-activated alkaline-earth metal halophosphate to produce nausea in certain attendant individuals is substantially eliminated.

2. The lamp of claim 1, wherein said europium-activated alkaline-earth metal halophosphate is strontium chlorophosphate activated with divalent europium.

3. The lamp of claim 2, wherein said strontium chlorophosphate is activated with divalent europium in an amount such that the gram-atom ratio of europium to europium plus strontium is from about 0.15 to 0.003.

4. The lamp of claim 1, wherein said second phosphor is a halophosphate.

5. The lamp of claim 4, wherein said halophosphate phosphor is a warm white halophosphate phosphor having a general constituent formulation of $3Ca(PO_4)_2\ Ca(F,Cl)_2\ 0.175Mn:0.015Sb$ and xy-C.I.E. coordinates of $x=0.440$ and $y=0.403$.

6. An improved method of an in vivo treatment of infants having hyperbilirubinemia, said method comprising, irradiating the infant subject with the emission produced by a lamp combination comprising at least one low pressure mercury-vapor discharge device having a coating of selected phosphors substantially comprising blue-radiating alkaline-earth metal halophosphate activated with divalent europium and a second phosphor with a color output that falls within an area of an xy-C.I.E. coordinate diagram, said area constituting a trapezium with corners at xy-C.I.E. coordinates (0.423, 0.370), (0.370, 0.410), (0.445, 0.550), (0.515, 0.484), with the weight ratio of said europium-activated alkaline-earth metal halophosphate to said second phosphor being from about 90:10 to 85:15, and shielding the eyes of said infant subject during the irradiation.

7. The method of claim 6, wherein said europium-activated alkaline-earth metal halophosphate is strontium chlorophosphate phosphor activated with divalent europium.

8. The method of claim 7, wherein said strontium chlorophosphate is activated with divalent europium in an amount such that the gram-atom ratio of europium to europium plus strontium is from about 0.15 to 0.003.

9. The method of claim 6, wherein said second phosphor is a halophosphate.

10. The method of claim 6, wherein said halophosphate phosphor has a general constituent formulation of $3Ca_3(PO_4)_2\cdot Ca(F,Cl)_2:0.175Mn:0.015Sb$ and xy-C.I.E. coordinates of $x=0.440$ and $y=0.403$.

* * * * *